United States Patent [19]
Klicek

[11] Patent Number: 5,472,442
[45] Date of Patent: Dec. 5, 1995

[54] MOVEABLE SWITCHABLE ELECTROSURGICAL HANDPIECE

[75] Inventor: Michael S. Klicek, Troy, Mich.

[73] Assignee: Valleylab Inc., Boulder, Colo.

[21] Appl. No.: 216,901

[22] Filed: Mar. 23, 1994

[51] Int. Cl.⁶ ................................................. A61B 17/36
[52] U.S. Cl. ............................... 606/42; 606/34; 606/45; 606/48
[58] Field of Search ..................... 606/37–42, 45–50, 606/51, 52

[56] References Cited

U.S. PATENT DOCUMENTS

| | | | |
|---|---|---|---|
| 4,041,952 | 8/1977 | Morrison, Jr. et al. | 606/52 |
| 4,051,855 | 10/1977 | Schneiderman | 606/37 |
| 4,244,371 | 1/1981 | Farin | 606/35 |
| 4,911,159 | 3/1990 | Johnson et al. | |
| 5,035,695 | 7/1991 | Weber, Jr. et al. | |
| 5,098,430 | 3/1992 | Fleenor | |

Primary Examiner—Stephen C. Pellegrino
Assistant Examiner—Michael Peffley
Attorney, Agent, or Firm—Peter C. Richardson; Lawrence C. Akers; Aaron Passman

[57] ABSTRACT

An active electrode switches from a monopolar mode extending from a handpiece and a patient return to a bipolar mode with the active and return electrodes extending. An active lead selectively connects the active output and the active electrode. A return lead selectively connects the return electrode and the return output in the monopolar mode or the return terminal when in the bipolar mode. Terminals connect with wiring to the electrodes to complete the circuit for the bipolar mode. One terminal is on the generator and one is in the handpiece to connect to the electrodes and complete the circuit for bipolar. The electrode has a control on the handpiece for the surgeon to change circuitry and to position the electrode for each mode. The return electrode in the monopolar mode is in the handpiece disconnected from its terminal. The return electrode connects to its terminal when extended from the handpiece but for monopolar a pair of patient pads connected to a monitoring circuit test continuity. A method of use has steps of switching the electrode from the monopolar to bipolar, providing the generator with outputs to the electrodes, having terminals for the electrodes when used for bipolar, including an active lead selectively in circuit between the active output and electrode and including a return lead selectively in circuit between the return electrode and output when monopolar or the terminal when bipolar.

10 Claims, 3 Drawing Sheets

FIG. 4
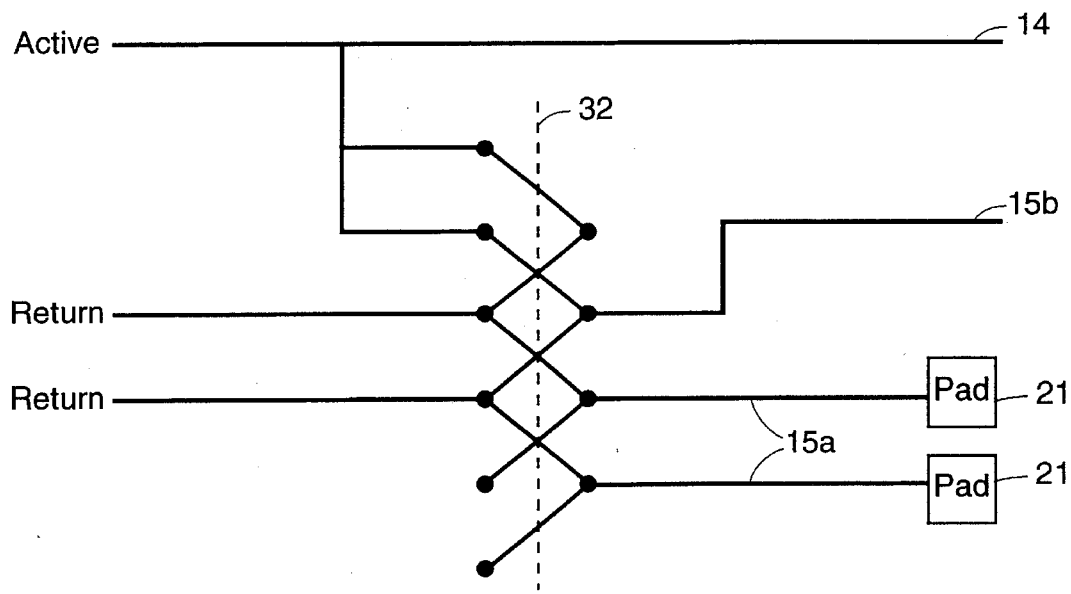
FIG. 5
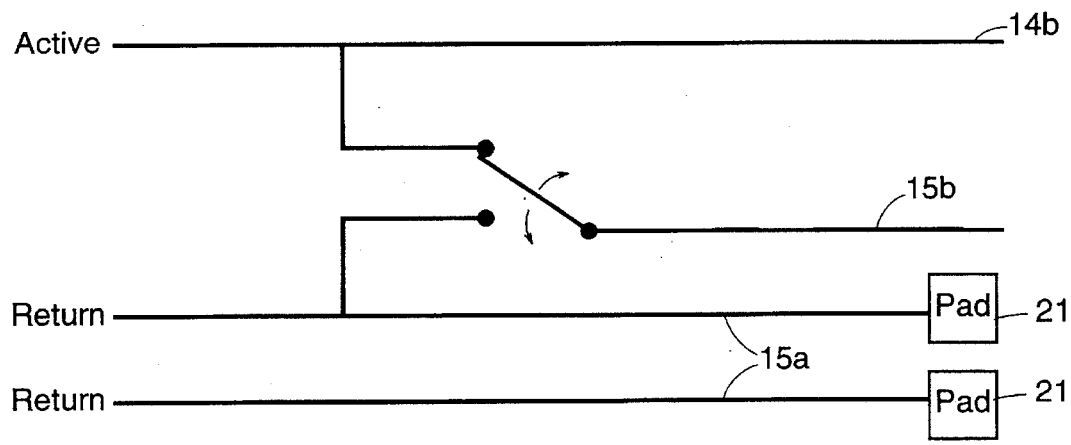
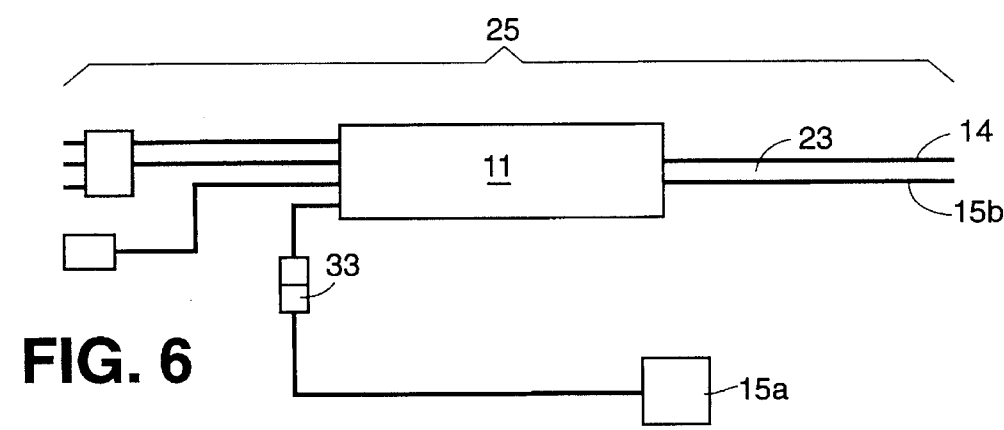
FIG. 6

MOVEABLE SWITCHABLE ELECTROSURGICAL HANDPIECE

FIELD OF THE INVENTION

Electrosurgery circuitry is monopolar or bipolar at the option of the surgeon through a convertible handpiece and techniques for the change.

BACKGROUND OF THE DISCLOSURE

Electrosurgery requires that the high frequency energy applied to a human or animal patient be return to the electrosurgical generator to avoid injury to the patient or surgeon. The application of a radio frequency electrical energy to a surgical site on the patient can be selected for tissue cutting, coagulation, or a blend thereof. In monopolar mode the radio frequency current that is generated by the electrosurgical generator is applied to tissue from an active electrode held by the surgeon, and is collected from a dispersive electrode or pad attached to the patient. A small contact area of the active electrode causes a high current density so that a spark enters the tissue at the surgical site. This spark causes intense localized heating, eschar, fulguration and other effects, to achieve the cutting and/or coagulation. The dispersive electrode collects the energy returning it to the electrosurgical generator to complete the electrical circuit. The dispersive electrode is of a significant size so that the energy density collected thereby is low enough to avoid any surgical or heating effect that would burn.

Burns develop when the power delivered to the tissue after passage through the body results in a high energy density at the exit because of localized tissue heating due to a high resistance connection. This situation happens when the energy is allowed to leave a human's body or animal's body at a poor dispersive electrode connection or a location other than the dispersive electrode. The later condition is called leakage. A burn from leakage can be quite severe as the patient when anesthetized will not react. The burn area is frequently covered so the doctor or surgical attendants will not see it until it is too late to take corrective action.

Another potential path for leakage burns is to the surgeon through contact with the active electrode handpiece or the conductors which supply the radio frequency, high voltage electrosurgical energy. Leakage in that circumstance may harm or burn the surgeon or one of the surgical attendants in contact with the active electrode handpiece or its supply conductor and any ground. It is for this reason that leakage or alternate path energy flow in electrosurgery are of considerable concern and efforts are made to monitor and control leakage.

An even worse condition occurs if the electrosurgical generator connection to the dispersive electrode is accidentally separated. Thus, with no direct energy path back to the electrosurgical generator, all of the power travels through any alternate grounded paths, such as through the monitoring electrodes, the surgeon and/or the surgical table. Severe burns are a possible result. At the relatively high frequencies of electrosurgical current, e.g., 500 kilohertz to 1 megahertz, stray capacitance to ground allows another ground referenced path. Furthermore, the amount of stray capacitance required to create this other significant path for ground referenced energy flow is not great.

Minimally invasive procedures include several trocars placed into the body for access to a cavity therein. One trocar could provide illumination and video, another insufflation and another minimally invasive operative instruments. Surgery through a trocar inserted opening through for example, the tissue of the abdominal wall has become an important means to minimize the extent of surgical invasion. The lessening of invasion improves the cosmetic result, shortens recovery and lowers the cost. Minimally invasive internal surgical procedures and equipment are available and in use for a variety of medical operations including gall bladder, bowel and gynecological surgery. A proper and simple instrument to selectively apply monopolar or bipolar electrosurgical effects through the opening is needed. In the minimally invasive setting, with as few as three instrument carrying openings or portals into the abdomen, the ability to treat tissue with either monopolar or bipolar systems on one handpiece is currently not feasible.

There is a wide variety of generic scissors and grasping forceps, as well as some slightly more specialized tools intended for grasping specific organs such as the gall bladder or bowel. Less invasive or minimally invasive surgical procedures are growing in frequency of use and complexity. Such procedures include: laparoscopy, thoracoscopy, endoscopy, etc.

If the surgeon had an easy way of switching between monopolar and bipolar surgery without removal of the handpiece, then the number of instruments and the time required to align the laparoscopic instrument during placement would be minimized. Monopolar electrosurgery is sometimes difficult and dangerous in a laparoscopic setting and bipolar surgery is limited with respect to the nature of the specific bipolar effectors being applied. Notwithstanding the aforesaid currently, disposable minimally invasive graspers and dissectors for laparoscopy account for millions in sales, with strong growth expected. U.S. Pat. No. 5,098,430 has a handpiece with a moveable active electrode used to selectively convert the instrument from a cutting tool when extended relative to a nozzle thereabout to a fulguration mode with the active electrode retracted relative to a nozzle thereabout. The disclosure is broadly directed to movement of the electrode although that construction is not specifically disclosed. A similar product is manufactured by Valleylab Inc of Boulder, Colo. as the model numbers E2531-6, E2532-6, E2580-28, E2581-28, E2582-28, E2583-28, E2580-36, E2581-36, E2582-36 and E2583-36 each having that have a moveable active electrode supported for axial movement coaxially within a nozzle for argon gas flow and model numbers E2718R-28, E2782R-28, E2783R-28, E2784R-28, E2787R-28, E2788R-28, E2718R-36, E2782R-36, E2783R-36, E2784R-36, E2787R-36 and E2788R-36 each having that have a moveable active electrode supported for axial movement coaxially within an elongated shaft of a laparoscopic instrument. The disclosure and claims herein are assigned to Valleylab Inc.

U.S. Pat. No. 4,911,159 has background that discloses a wide range of handpiece switch arrangements for changing between cutting and coagulation. It is customary current practice that electrosurgical generators have an industry accepted standard spacing for the output terminals for receiving the monopolar and bipolar leads so that handpiece and leads are interchangeable. Consequently, it is preferred that the hand switching between monopolar and bipolar by on a handpiece that is interchangeable, i.e. not requiring a special generator and able to function as an accessory for existing generators.

The knowledge of skilled artisans at the time of this disclosure of a monopolar or bipolar handpiece convertible at the option of the surgeon and techniques for the change is thus negligible.

SUMMARY OF THE INVENTION

An electrosurgical system for a surgeon has a handpiece preferably with a moveable switchable electrode for delivery of high frequency electrosurgical energy to an operational site on a patient. The moveable switchable electrode is preferably switchable from a first monopolar mode with an active electrode carried extending from the handpiece and a return electrode attached to the patient to a second bipolar mode in which the active electrode and return electrode extend from the handpiece in position relative to each other to effect the operational site thereby. An electrosurgical generator has at least a pair of monopolar outputs for supplying electrosurgical energy to the active and return electrodes.

A pair of bipolar terminals of the electrosurgical generator supply electrosurgical energy to the active and return electrodes when used in the second bipolar mode. An active lead selectively in circuit between the active output and the active electrode. A return lead is selectively in circuit between the return electrode and the return output when in the first monopolar mode or the return terminal when in the second bipolar mode so the moveable switchable electrode may be modified at the handpiece by the surgeon to function in either the first monopolar mode or second bipolar mode.

The pair of bipolar terminals are most preferably on the electrosurgical generator and one or both are selectively connected through wiring to the active or return electrodes in the handpiece to complete the circuitry for the second bipolar mode. At least one of the pair of bipolar terminals is on the electrosurgical generator and the other terminal is preferably located within the handpiece for selective connection to either the active or return electrodes to complete the circuitry for the second bipolar mode.

The moveable switchable electrode has a control on the handpiece that is preferably accessible by the surgeon. The control permits selective changes in circuitry to position the moveable switchable electrode for conversion between the first monopolar mode and the second bipolar mode. The control joins to the return electrode and the control and return electrode are moveably supported by the handpiece to function as a unit. The return electrode during the first monopolar mode is preferably positioned inside the handpiece and is disconnected from its terminal. The return electrode connects to its terminal when extended outside the handpiece into a position adjacent to the active electrode by the surgeon's use of the control.

The return electrode has in one from of the system, when used in the first monopolar mode, a pair of pads that may preferably be attached to the patient. Each of the pads are separately connected to a monitoring circuit for testing continuity between each pad and the patient. The handpiece may include an elongated support extending distally for use within laparoscopic or endoscopic settings including trocars, body cavities or body orifices.

A method of using an electrosurgical system for surgery has steps including providing a handpiece having a moveable switchable electrode for delivery of high frequency electrosurgical energy to an operational site on a patient. Switching the moveable switchable electrode from a first monopolar mode with an active electrode carried extending from the handpiece and a return electrode attached to the patient to a second bipolar mode in which the active electrode and return electrode extend from the handpiece in position relative to each other to effect the operational site thereby is another step. A further step may be providing an electrosurgical generator having at least a pair of monopolar outputs for supplying electrosurgical energy to the active and return electrodes. Having on the electrosurgical generator a pair of bipolar terminals with electrosurgical energy to the active and return electrodes when used in the second bipolar models yet another step of the method. Including an active lead selectively in circuit between the active output and the active electrode is one more step. Preferably including a return lead selectively in circuit between the return electrode and the return output when in the first monopolar mode or the return terminal when in the second bipolar mode is a step that allows the moveable switchable electrode to be modified at the handpiece by the surgeon to function in either the first monopolar mode or second bipolar mode.

An electrosurgical accessory for a surgeon may have a handpiece with a moveable switchable electrode for delivery of high frequency electrosurgical energy to an operational site on a patient. The moveable switchable electrode is switchable from a first monopolar mode with an active electrode carried extending from the handpiece and a return electrode attached to the patient to a second bipolar mode in which the active electrode and return electrode extend from the handpiece in position relative to each other to effect the operational site thereby.

The moveable switchable electrode preferably has a control on the handpiece and accessible by the surgeon which control permits selective changes in circuitry and position of the moveable switchable electrode for conversion between the first monopolar mode and the second bipolar mode.

BRIEF DESCRIPTION OF THE DRAWINGS

FIG. 4 is a schematic diagram of another circuit that may be used in connection with return electrode monitoring of pads and for shifting from the first monopolar mode to the second bipolar mode.

FIG. 5 is a schematic circuit diagram of yet another switch used in a further alternate circuit to that of FIG. 4 for connecting a pair of return electrode monitoring pads with the movable switchable electrode of the handpiece.

FIG. 6 is a schematic circuit diagram illustrating the connections between the handpiece and the return electrode pad of a still further electrosurgical system when in the first monopolar mode.

DETAILED DESCRIPTION OF THE INVENTION

Figure 1:
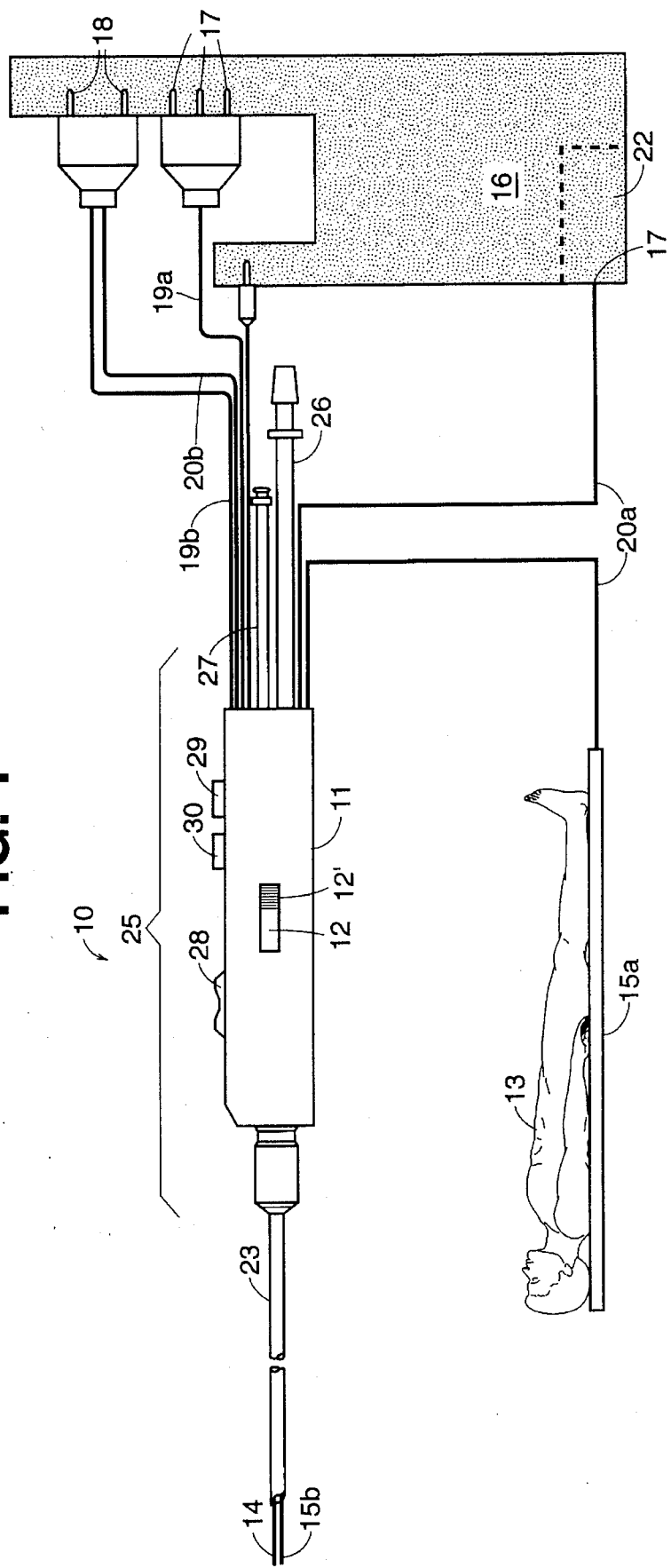
FIG. 1 is a schematic view of the circuit for the electrosurgical system wherein the handpiece is shown in some detail and the electrosurgical generator and return circuit is shown as blocks.

In FIG. 1, an electrosurgical system 10 for a surgeon has a handpiece 11 with a moveable switchable electrode 12 for delivery of high frequency electrosurgical energy to an operational site on a patient 13. The moveable switchable electrode 12 is switchable from a first monopolar mode with an active electrode 14 carried extending from the handpiece as shown in FIG. 1 and a return electrode 15a attached to the patient to a second bipolar mode in which the active electrode 14 and a return electrode 15b extends (shown by broken lines) from the handpiece 11 and in position relative to each other to effect the operational site thereby with bipolar electrosurgery. An electrosurgical generator 16 has at least a pair of monopolar outputs 17 for supplying electrosurgical energy to the active electrode 14 and return electrodes 15 a and/or 15b.

A pair of bipolar terminals 18 of the electrosurgical generator 16 supply electrosurgical energy to the active and return electrodes 14 and 15b when used in the second bipolar mode. At least an active lead 19a selectively in circuit between the active output 17 and the active electrode 14. A return lead 20a or 20b is selectively in circuit between the return electrode 15a or 15b, respectively, and the return output 17 when in the first monopolar mode or the return terminal 18 when in the second bipolar mode so the moveable switchable electrode 15b may be modified at the handpiece 11 by the surgeon to function in either the first monopolar mode or second bipolar mode.

The pair of bipolar terminals 18 are on the electrosurgical generator 16 and one or both are selectively connected through wiring 19b and 20b to the active 14 or return electrodes 15b in the handpiece 14 to complete the circuitry for the second bipolar mode. At least one of the pair of bipolar terminals 18 is on the electrosurgical generator and the other terminal is located within the handpiece 11 for selective connection to either the active 14 or return electrodes 15b to complete the circuitry for the second bipolar mode.

The moveable switchable electrode 15b has a control 12' on the handpiece 11 that is accessible by the surgeon. The control 12' permits selective changes in circuitry to position the moveable switchable electrode 15b for conversion between the first monopolar mode and the second bipolar mode. The control 12' joins to the return electrode 15a or 15b and the control 12' and return electrode 15a or 15b are moveably supported by the handpiece 11 to function as a unit. The return electrode 15a during the first monopolar mode is positioned inside the handpiece 11 and is disconnected from its terminal 17. The return electrode 15a connects to its terminal 17 when extended outside the handpiece 11 into a position adjacent to the active electrode 14 by the surgeon's use of the control 12'.

The return electrode 15a has in one form of the system, when used in the first monopolar mode, a pair of pads 21 that may be attached to the patient 13. Each of the pads 21 are separately connected to a monitoring circuit 22 for testing continuity between each pad 21 and the patient 17. The handpiece 11 in an alternate embodiment includes an elongated support 23 extending distally for use within laparoscopic or endoscopic settings including trocars, body cavities or body orifices.

A method of using an electrosurgical system 10 for surgery has steps including providing a handpiece 11 having the moveable switchable electrode 12 for delivery of high frequency electrosurgical energy to an operational site on a patient 13. Switching the moveable switchable electrode from the first monopolar mode with the active electrode 14 carried extending from the handpiece 11 and the return electrode 15a attached to the patient to the second bipolar mode in which the active electrode 14 and the return electrode 15b extend from the handpiece 11 in juxtaposed position relative to each other to effect the operational site thereby is another step. A further step may be providing the electrosurgical generator 16 having at least the pair of monopolar outputs 17 for supplying electrosurgical energy to the active electrode 14 and return electrode 15a. Having on the electrosurgical generator 16 the pair of bipolar terminals 18 with electrosurgical energy to the active electrode 14 and return electrode 15b when used in the second bipolar mode is yet another step of the method. Including the active lead 19a selectively in circuit between the active output 17 and the active electrode 14 is one more step. Including the return lead 20a selectively in circuit between the return electrode 15a or 15b and the return output 17 when in the first monopolar mode or the return terminal 18 when in the second bipolar mode is a step that allows the moveable switchable electrode 12 to be modified at the handpiece 11 by the surgeon to function in either the first monopolar mode or second bipolar mode. An electrosurgical accessory 25 for a surgeon may have a handpiece 11 with a moveable switchable electrode 12 for delivery of high frequency electrosurgical energy to an operational site on a patient 13. The moveable switchable electrode 12 is switchable from a first monopolar mode with an active electrode 14 carried extending from the handpiece 11 and a return electrode 15a attached to the patient 13 to a second bipolar mode in which the active electrode 14 and return electrode 15b extends from the handpiece 11 in position relative to each other to effect the operational site thereby. The moveable switchable electrode 12 has a control 12' on the handpiece 11 and accessible by the surgeon which control 12' permits selective changes in circuitry and position of the moveable switchable electrode 12 for conversion between the first monopolar mode and the second bipolar mode.

FIG. 1 is a full side view of the electrosurgical system 10 and the handpiece 11. Various arrangements can produce alternate systems which will provide the desired ability to convert between monopolar and bipolar modes. Many changes can be made. The circuitry to the electrosurgical generator 11 and the respective patient pad 15a or 21 may take many forms. The position of the monopolar bipolar control 12' and its connection may be varied to suit the handpiece 11 or surgical application.

The disclosure herein seeks to explain several alternatives. In general the claims herein broadly protect the accessory 25 system 10 and its method of use that permit the moveable switchable electrode 12 to convert by preferably moving inwardly and outwardly axially relative to the handpiece 11. Moreover the control 12' while described as manually activated by the surgeon can also be electrical (solenoid), hydraulic (piston and cylinder) or latched and spring loaded. The bipolar return electrode 15b could be fixed or idle and in that circumstance only its electrical connection would be changed by the control 12' when bipolar surgery is desired. It should be noted that if laparoscopic or endoscopic surgical systems are preferred then the elongate support 23 compatible with a 5 mm or 10 mm trocar may be used with the addition of suction and irrigation as desired.

The moveable switchable electrode 12 which allows the handpiece 11 to be convertible from the first monopolar mode to the second bipolar mode is a part of the protection sought to be covered by the claims. The system 10 may include suction and/or irrigation channels 26 and 27 in FIG. 1. The handpiece 11 is thus capable of electrically and mechanically connecting to the moveable switchable electrode 12 and is preferably able to lock the return electrode 15b in the second mode extended position unless idle wherein it may always be extended.

The handpiece 11 may include integral channels for suction 26 and irrigation 27. When the handpiece 11 has the moveable switchable electrode 12; the control 12' must embody not only the user interface but also electrode guidance for the safety and secure axial motion. The handpiece 11 will include switches 28 to activate the cut and coag functions of the electrosurgical generator 16.

Figure 2A:
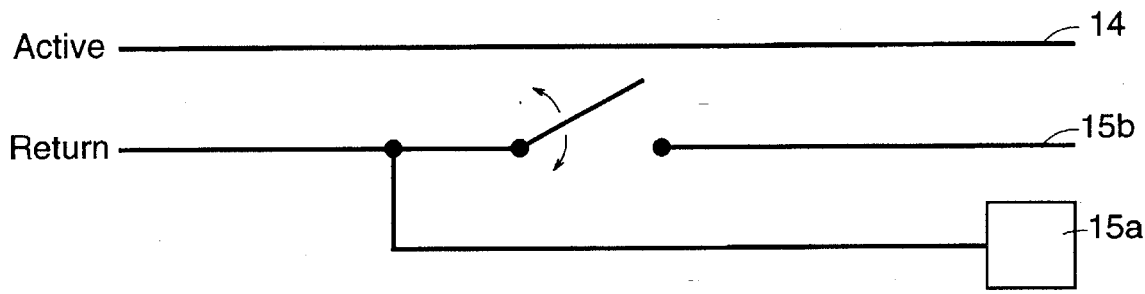
FIG. 2 are two schematic circuit diagrams showing the relationship of the switching as alternate versions of the same approach.
Figure 2B:
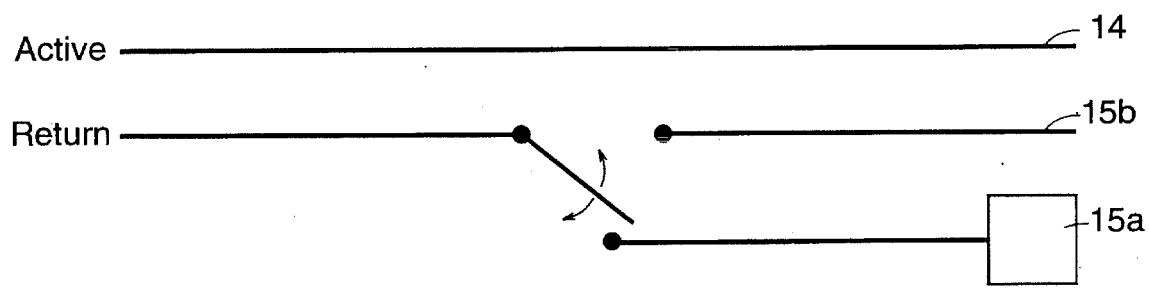

The handpiece 11 has switching to change the active electrode 14 and return electrode 15a or (idle) return electrode 15b from the first monopolar mode to the second bipolar mode. In one arrangement the handpiece 11 should also contain buttons for the suction 29 and irrigation 30 functions. The electrical circuitry to switch between the first and second modes may be in an alternate version separate from the mechanical movement of the return electrode 15b. Electrical switching within handpiece to connect between monopolar and bipolar may take many forms:

(1) A simple embodiment of the concept is schematically illustrated in FIG. 2; it has the active electrode 14 and the return electrode 15a or 15b in circuit with the patient 13 and when there is no current flow to the return electrode pad 15a from active electrode 14 or idle bipolar 15b electrode when set for the second bipolar mode.

Figure 3:
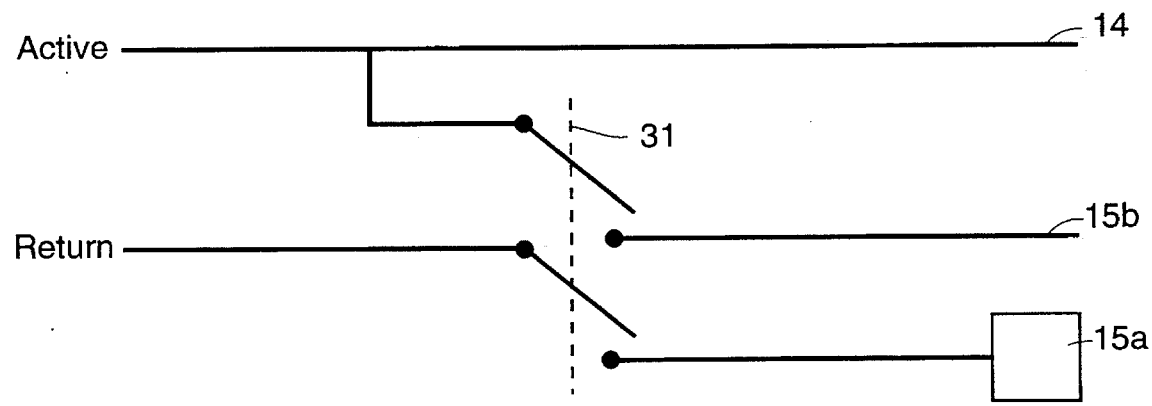
FIG. 3 is a schematic circuit diagram of an alternate version of a switch for shifting the return electrode from a first monopolar mode to a second bipolar mode.

(2) FIG. 3 is the handpiece 11 of increased complexity to avoid the transfer of energy to the return electrode pad 15a when in the second bipolar mode as the return pad plugs into the handpiece 11 and the return lead plugs into the patient return output 17 of the electrosurgical generator 16. In FIG. 4 the system 10 having the return electrode monitor 22 (herein REM) there are two return leads 20a from two electrode pads 21 or 15b. Several U.S. Patents, assigned to the Valleylab the assignee of this disclosure include U.S. Pat. Nos. 4,200,104; 4,416, 276 and 4,416,277; are incorporated herein by reference and made a part hereof insofar as they describe and explain REM systems.

(3) In FIG. 3 double throw double pole switch 31 has the following advantages:

(a) In the second bipolar mode the patient return electrode pad 15a is not connected to the electrosurgical generator 16 eliminating all concerns about "leakage" current to the return pad 15a from the bipolar surgical site.

(b) In the first monopolar mode, the active electrode 14 and the return electrode 15b are common which is an advantage if return electrode is idle (not moveable, i.e. non retractable in the first monopolar mode).

Thus the active electrode 14 or the return electrode 15b can be used in the first monopolar mode; higher power levels used in the first monopolar mode require increased insulation so this approach may be preferred for the system 10.

The moveable switchable electrode 12 may accommodate the REM pad system in the first monopolar mode. The particular switch 32 shown schematically in FIG. 4 could be a four pole two position switch 32. A slide control 12' may be the preferred commercial implementation for user friendly interface of such a complex switch 32. The switch 32 is shown in the second bipolar mode the return electrode 15a makes contact with the output 17 return for the REM pad at the electrosurgical generator 16. The patient pad lead 20a between the handpiece 11 and the electrosurgical generator 16 is thus opened, see FIG. 4 dashed lines in FIG. 4. The solid lines show the switch in the first monopolar mode. The return electrode 15a is connected to the active electrode 14 and the return electrode pad (both leads) are respectively connected to the two leads 20a of the electrosurgical generator 16 return output 17. When the handpiece control 12' is moved from the first monopolar mode to the second bipolar mode, a REM alarm can if desired be connected to sound. In addition, because that embodiment is connected to the monopolar outputs of the electrosurgical generator 16, a dual REM pad is not indicated. Since a REM alarm will remain until the two patient return leads 21a are no longer together in the bipolar configuration.

Suction and irrigation sources are not shown. The possible sets of wiring required include the active output wiring harness with monopolar active and return leads 19a and 20a fixed to the handpiece 11. A dual wire patient return harness that plugs into electrosurgical generator 16 patient return output 17 fixed to handpiece 11.

The three wire sets 19a, 20a, 19b and 20b and the suction 26 and irrigation 27 make the harness with five parts. That and the bulk of the harness may be too many for user acceptance. Re-examination of the alternatives discussed shows the following system 10 possibilities. It is assumed that the convertible monopolar bipolar handpiece 11 with the movable switchable electrode 12 is preferably REM compatible in the first monopolar mode. Consequently, in the second bipolar mode (as the system 10 is presently arranged) the integrity of the REM system must be maintained, an embodiment of that is in FIG. 5. It is possible that some current to the return electrode 15a may exist and to maintain REM system integrity, only one side of the return patient output 17 will see active current flow. A variation of the circuit of FIG. 5 is shown in FIG. 6; it includes a shunt 33 within the handpiece 11 and between the active electrode 14 and return electrodes 15b when in the first monopolar mode to maintaining system integrity.

What is claimed is:

1. An electrosurgical system with a circuit having an electrosurgical generator with at least a pair of monopolar active and return outputs for supplying electrosurgical energy to electrodes in a first monopolar mode, and a pair of bipolar terminals electrically coupled to the electrosurgical generator for supplying electrosurgical energy to electrodes when used in a second bipolar mode, the electrosurgical system for a surgeon to use on a surgical site comprising:

a handpiece for the surgeon to hold;

a moveable switchable electrode extendably carried on the handpiece for motion relative thereto which moveable switchable electrode is switchable when extended by the surgeon to act as a return electrode positionable relative to and active electrode to effect the operational site when positioned therebetween;

an active electrode carried on the handpiece;

a return attached to the patient for use in the first monopolar mode;

means for mounting the moveable switchable electrode on the handpiece for allowing switching the moveable switchable electrode from the first monopolar mode with an active electrode carried extending from the handpiece and the return attached to the patient, to the second bipolar mode in which the active electrode and return electrode extend from the handpiece in position relative to each other to effect the operational site thereby;

an active lead selectively in circuit between the active output and the active electrode, and a return lead selectively in circuit between the return attached to the patient and the return output when in the first monopolar mode or the return terminal and the return electrode when in the second bipolar mode so the moveable switchable electrode may be modified at the handpiece by the surgeon to function in either the first monopolar mode or second bipolar mode from the first monopolar mode with an active electrode carried extending from the handpiece and a return attached to the patient to a second bipolar mode in which the active electrode and return electrode extend from the handpiece in position relative to each other to effect the operational site thereby.

2. The electrosurgical system of claim 1 wherein the pair of bipolar terminals are on the electrosurgical generator and one is selectively connected through wiring to the return for the first monopolar mode or the return electrode in the handpiece to complete the circuitry for the second bipolar mode.

3. The electrosurgical system of claim 1 wherein at least one of the pair of bipolar terminals is physically positioned on the electrosurgical generator and the other terminal is located within the handpiece for selective connection to either the return for the first monopolar mode or the return electrode to complete the circuitry for the second bipolar mode.

4. The electrosurgical system of claim 1 wherein the moveable switchable electrode has a control on the handpiece that is accessible by the surgeon, the control permits selective changes in circuitry and allows positioning the moveable switchable electrode for conversion between the first monopolar mode and the second bipolar mode.

5. The electrosurgical system of claim 3 wherein the control joins to the return electrode, and the control and the return electrode are moveably supported on the handpiece to function as a unit, the return electrode during the first monopolar mode is positioned inside the handpiece and is disconnected from its terminal therein, the return electrode connects to its terminal therein when extended outside the handpiece into a position adjacent to the active electrode by the surgeon's use of the control.

6. The electrosurgical system of claim 1 wherein the return electrode is a pair of pads in the first monopolar mode, the pair pads for attachment to the patient, each of the pads are separately connected to a monitoring circuit for testing continuity between each pad and the patient.

7. The electrosurgical system of claim 1 wherein the handpiece includes an elongated support extending distally for use within laparoscopic or endoscopic settings including trocars, body cavities or body orifices.

8. A method of using an electrosurgical system with a circuit having an electrosurgical generator with at least a pair of monopolar outputs for supplying electrosurgical energy to electrodes and a pair of bipolar terminals on the electrosurgical generator for supplying electrosurgical energy to electrodes when used in the second bipolar mode, the electrosurgical system for a surgeon to use on a surgical site for surgery comprising steps of:

providing a handpiece having a moveable switchable electrode for delivery of high frequency electrosurgical energy to an operational site on a patient;

switching the moveable switchable electrode from a first monopolar mode with an active electrode carried extending from the handpiece and a return electrode attached to the patient to a second bipolar mode in which the active electrode and an idle return electrode extends from the handpiece in position relative to each other to effect the operational site thereby;

including an active lead selectively in circuit between the active output and the active electrode, and including a return lead selectively in circuit between the return electrode and the return output when in the first monopolar mode or the return terminal when in the second bipolar mode so the moveable switchable electrode may be modified at the handpiece by the surgeon to function in either the first monopolar mode or second bipolar mode by selective connection of the return electrode or the idle electrode.

9. An electrosurgical accessory for use with an electrosurgical generator supplying high frequency electrosurgical energy through an active electrode and an electrical return, for use by a surgeon for electrosurgical treatment of a patient's operational site, the accessory comprising:

a handpiece having a switchable electrode for connection of high frequency electrosurgical energy to an operational site on a patient, which switchable electrode is switchable from a first monopolar mode with the active electrode carried extending from the handpiece and the electrical return attached to the patient, to a second bipolar mode wherein the electrical return is the switchable electrode;

a switching means locate on the handpiece allowing the electrosurgical accessory to be used in a first monopolar mode between the active electrode and the electrical return, or an a second bipolar mode wherein the active electrode and the switchable electrode extend for bipolar use.

10. The electrosurgical accessory of claim 9 wherein the switchable electrode has a control on the handpiece and accessible by the surgeon which control permits selective changes in circuitry of the switchable electrode for conversion between the first monopolar mode and the second bipolar mode.

* * * * *